(12) United States Patent
Viscomi et al.

(10) Patent No.: US 10,285,944 B2
(45) Date of Patent: *May 14, 2019

(54) GASTRORESISTANT PHARMACEUTICAL FORMULATIONS CONTAINING RIFAXIMIN

(71) Applicant: ALFASIGMA S.P.A., Milan (MI) (IT)

(72) Inventors: Giuseppe Claudio Viscomi, Bologna (IT); Ernesto Palazzini, Bologna (IT); Villiam Zamboni, Bologna (IT); Maria Rosaria Pantaleo, Bologna (IT)

(73) Assignee: ALFASIGMA S.P.A., Milan (MI) (IT)

( * ) Notice: Subject to any disclaimer, the term of this patent is extended or adjusted under 35 U.S.C. 154(b) by 132 days.

This patent is subject to a terminal disclaimer.

(21) Appl. No.: 14/044,844

(22) Filed: Oct. 2, 2013

(65) Prior Publication Data

US 2014/0112987 A1    Apr. 24, 2014

Related U.S. Application Data

(63) Continuation of application No. 11/814,628, filed as application No. PCT/EP2006/002022 on Mar. 6, 2006, now Pat. No. 8,568,782.

(30) Foreign Application Priority Data

Mar. 7, 2005 (IT) .............................. BO2005A0123

(51) Int. Cl.
| | |
|---|---|
| *A61K 31/395* | (2006.01) |
| *A61K 31/437* | (2006.01) |
| *A61K 9/16* | (2006.01) |
| *A61K 9/28* | (2006.01) |
| *A61K 9/00* | (2006.01) |
| *A61K 9/20* | (2006.01) |
| *A61K 31/44* | (2006.01) |
| *A61K 9/50* | (2006.01) |

(52) U.S. Cl.
CPC .......... *A61K 9/1652* (2013.01); *A61K 9/0095* (2013.01); *A61K 9/1635* (2013.01); *A61K 9/2027* (2013.01); *A61K 9/2054* (2013.01); *A61K 9/28* (2013.01); *A61K 9/5026* (2013.01); *A61K 9/5073* (2013.01); *A61K 31/395* (2013.01); *A61K 31/437* (2013.01); *A61K 31/44* (2013.01)

(58) Field of Classification Search
None
See application file for complete search history.

(56) References Cited

U.S. PATENT DOCUMENTS

| | | | |
|---|---|---|---|
| 5,356,625 A | 10/1994 | Ying | |
| 5,401,512 A * | 3/1995 | Rhodes | A61K 9/4891 424/458 |
| 5,840,332 A | 11/1998 | Lerner et al. | |
| 6,090,411 A * | 7/2000 | Pillay | A61K 9/0065 424/468 |
| 6,322,819 B1 * | 11/2001 | Burnside | A61K 9/5026 424/472 |
| 7,045,620 B2 | 5/2006 | Viscomi et al. | |
| 7,585,838 B2 | 9/2009 | Lin et al. | |
| 7,605,240 B2 | 10/2009 | Lin et al. | |
| 7,612,199 B2 | 11/2009 | Viscomi et al. | |
| 7,902,206 B2 | 3/2011 | Viscomi et al. | |
| 7,906,542 B2 | 3/2011 | Viscomi et al. | |
| 7,915,275 B2 | 3/2011 | Viscomi et al. | |
| 7,923,553 B2 | 4/2011 | Viscomi et al. | |
| 7,928,115 B2 | 4/2011 | Forbes et al. | |
| 8,158,644 B2 | 4/2012 | Viscomi et al. | |
| 8,158,781 B2 | 4/2012 | Viscomi et al. | |
| 8,173,801 B2 | 5/2012 | Viscomi et al. | |
| 8,193,196 B2 | 6/2012 | Viscomi et al. | |
| 8,197,805 B2 | 6/2012 | Lin et al. | |
| 8,217,054 B2 | 7/2012 | Maffei et al. | |
| 8,318,763 B2 | 11/2012 | Viscomi et al. | |
| 8,404,704 B2 | 3/2013 | Viscomi et al. | |
| 8,518,949 B2 | 8/2013 | Viscomi et al. | |
| 8,568,782 B2 | 10/2013 | Viscomi et al. | |
| 8,980,872 B2 | 3/2015 | Tamaoki et al. | |
| 2002/0107200 A1 | 8/2002 | Chang et al. | |
| 2003/0059471 A1 | 3/2003 | Compton et al. | |
| 2003/0157174 A1 | 8/2003 | Tsukuda et al. | |
| 2004/0170617 A1 * | 9/2004 | Finegold | A61K 31/43 424/93.45 |
| 2005/0008651 A1 | 1/2005 | Jestin et al. | |
| 2005/0101598 A1 * | 5/2005 | Viscomi | C07D 498/22 514/224.5 |
| 2005/0196418 A1 | 9/2005 | Yu et al. | |
| 2005/0272754 A1 | 12/2005 | Viscomi et al. | |
| 2008/0262012 A1 | 10/2008 | Viscomi et al. | |
| 2008/0262024 A1 | 10/2008 | Viscomi et al. | |
| 2009/0324736 A1 | 12/2009 | Johnson et al. | |
| 2010/0317681 A1 | 12/2010 | Forbes | |
| 2010/0330129 A1 | 12/2010 | Viscomi et al. | |
| 2011/0086871 A1 | 4/2011 | Viscomi et al. | |
| 2011/0118295 A1 | 5/2011 | Forbes et al. | |
| 2011/0178113 A1 | 7/2011 | Forbes et al. | |
| 2012/0035202 A1 | 2/2012 | Viscomi et al. | |
| 2012/0202989 A1 | 8/2012 | Viscomi et al. | |

(Continued)

FOREIGN PATENT DOCUMENTS

| | | |
|---|---|---|
| EP | 0161534 B1 | 9/1989 |
| EP | 0513513 B1 | 5/1991 |

(Continued)

OTHER PUBLICATIONS

Physicians' Desk Reference, pp. 2790-2791, 62, Thomson Healthcare, Montvale XP002601190 (2007).

(Continued)

*Primary Examiner* — Bong-Sook Baek
(74) *Attorney, Agent, or Firm* — Steinfl + Bruno LLP (57) ABSTRACT

The object of the invention consists of pharmaceutical formulations containing rifaximin in the shape of microgranules made gastroresistant by an insoluble polymer at pH values between 1.5 and 4.0 and soluble at pH values between 5.0 and 7.5, by their preparation and by their use in the manufacture of medicinal preparations useful in the treatment of inflammatory bowel diseases (IBD) and mainly Crohn's disease.

44 Claims, 4 Drawing Sheets

(56) References Cited

U.S. PATENT DOCUMENTS

| | | | |
|---|---|---|---|
| 2012/0203000 A1 | 8/2012 | Viscomi et al. |
| 2012/0214989 A1 | 8/2012 | Viscomi et al. |
| 2012/0245192 A1 | 9/2012 | Viscomi et al. |
| 2013/0004576 A1 | 1/2013 | Viscomi et al. |
| 2013/0028971 A1 | 1/2013 | Viscomi et al. |
| 2013/0072676 A1 | 3/2013 | Maffei et al. |
| 2013/0164384 A1 | 6/2013 | Johnson et al. |
| 2013/0184302 A1 | 7/2013 | Bortey et al. |
| 2013/0281697 A1 | 10/2013 | Viscomi et al. |
| 2013/0287692 A1 | 10/2013 | Viscomi et al. |
| 2013/0289269 A1 | 10/2013 | Viscomi et al. |
| 2013/0310410 A1 | 11/2013 | Viscomi et al. |
| 2014/0235662 A1 | 8/2014 | Viscomi et al. |
| 2015/0073007 A1 | 3/2015 | Viscomi et al. |
| 2015/0080421 A1 | 3/2015 | Viscomi et al. |

FOREIGN PATENT DOCUMENTS

| | | |
|---|---|---|
| EP | 0547294 B1 | 8/1992 |
| EP | 0547294 A1 | 6/1993 |
| EP | 0547294 B1 | 6/1993 |
| EP | 0616808 A1 | 3/1994 |
| EP | 0616808 A1 | 9/1994 |
| EP | 0616808 B1 | 9/1994 |
| EP | 0935417 B1 | 8/1999 |
| EP | 1557421 A1 | 7/2005 |
| EP | 1557421 B1 | 7/2005 |
| EP | 1676847 A1 | 7/2006 |
| EP | 1676847 B1 | 7/2006 |
| EP | 1676848 B1 | 7/2006 |
| EP | 1698630 A1 | 9/2006 |
| EP | 1698630 B1 | 9/2006 |
| EP | 1 874 273 | 1/2008 |
| EP | 2011486 A1 | 1/2009 |
| EP | 2059232 | 5/2009 |
| EP | 2208730 A1 | 7/2010 |
| EP | 2210893 A1 | 7/2010 |
| EP | 2420226 A1 | 2/2012 |
| EP | 1874273 B1 | 1/2013 |
| EP | 2542225 B1 | 8/2014 |
| EP | 2421869 B1 | 3/2015 |
| EP | 2059232 B1 | 4/2017 |
| EP | 2618819 B1 | 11/2017 |
| GB | 1317830 A | 5/1973 |
| GB | 2079270 A | 1/1982 |
| IT | BO 2005 A 000123 A | 3/2005 |
| IT | MI2006A001692 A1 | 3/2008 |
| WO | 2005/044823 A2 | 5/2005 |
| WO | 2005044823 A2 | 5/2005 |
| WO | 2006/008512 A2 | 1/2006 |
| WO | 2006/094737 A2 | 9/2006 |
| WO | 2006094143 A2 | 9/2006 |
| WO | 2006094144 A2 | 9/2006 |
| WO | 2006094181 A2 | 9/2006 |
| WO | 2006094662 A1 | 9/2006 |
| WO | 2007103448 A2 | 9/2007 |
| WO | 2007130882 A2 | 11/2007 |
| WO | 2007130893 A2 | 11/2007 |
| WO | 2008016708 A2 | 2/2008 |
| WO | 2008/029208 A1 | 3/2008 |
| WO | 2008029208 A1 | 3/2008 |
| WO | 2009008005 A1 | 1/2009 |
| WO | 2009008006 A2 | 1/2009 |
| WO | 2009047801 A1 | 4/2009 |
| WO | 2009052255 A2 | 4/2009 |
| WO | 2009108814 A1 | 9/2009 |
| WO | 2009137672 A1 | 11/2009 |
| WO | 2010035751 A1 | 4/2010 |
| WO | 2010044093 A1 | 4/2010 |
| WO | 2010093776 A1 | 8/2010 |
| WO | 2010122436 A1 | 10/2010 |
| WO | 2010144865 A2 | 12/2010 |
| WO | 2010148040 A1 | 12/2010 |
| WO | 2011032085 A1 | 3/2011 |
| WO | 2011/051971 A2 | 5/2011 |
| WO | 2011050397 A1 | 5/2011 |
| WO | 2011061516 A2 | 5/2011 |
| WO | 2011061519 A2 | 5/2011 |
| WO | 2011088688 A1 | 7/2011 |
| WO | 2011103246 A1 | 8/2011 |
| WO | 2011107970 A2 | 9/2011 |
| WO | 2011110930 A2 | 9/2011 |
| WO | 2012009387 A1 | 1/2012 |
| WO | 2012009388 A1 | 1/2012 |
| WO | 2012035283 A1 | 3/2012 |
| WO | 2012038898 A1 | 3/2012 |
| WO | 2012076832 A1 | 6/2012 |
| WO | 2013017928 A1 | 2/2013 |
| WO | 2013067394 A1 | 5/2013 |
| WO | 2014186675 A1 | 11/2014 |

OTHER PUBLICATIONS

Rifaximin, European Pharmacopoeia Ed. 6.5 pp. 4955-4957 (2009).
Rifaximin, European Pharmacopoeia 7.1 pp. 3459-3460 (2011).
Infante R.M. et al., Enteroaggregative *Escherichia coli* diarrhea in travelers: Response to Rifaximin Therapy, Clin. Gastroenterol. Hepatol. pp. 135-138, vol. 2, No. 2, (2004).
Lochs H. et al., A New Extended Intestinal Release Formulation of Rifaximin, 400 Mg Tablets, for the Treatment of Moderately Active Crohn's Disease, Digestive Disease Week 2011, Chicago, Poster Mo1164, (2011).
Prantera C. et al., Antibiotic treatment of Crohn's disease: results of a multicentre, double blind, randomized, placebo-controlled trial with rifaximin., pp. 1117-1125, 23 (8), Aliment. Pharmacol. Ther. (2006).
Prantera C. et al., Rifaximin-EIR treatment in Crohn's disease—RETIC/03/06 Study—Oral communication, UEGW, Oct. 23-27, 2010—Barcelona, Spain.
Prantera C. et al., Rifaximin and Crohn's disease., World J. Gastroenterol., 19 (42), pp. 7487-7488 (2013).
Shafran I. et al., Adjunctive Antibiotic Therapy With Rifaximin May Help Reduce Crohn's Disease Activity., Dig. Dis. Sci. pp. 1079-1084, 55 (4) (2010).
Shafran I. et al., An open-label evaluation of rifaximin in the treatment of active Crohn's disease, 21 (8), Curr. Med. Res. Opin. pp. 1165-1169, (2005).
Steffen R. et al., Therapy of Travelers' Diarrhea With Rifaximin on Various Continents, Am. J. Gastroenterol. vol. 98 (5), pp. 1073-1078 (2003).
Viscomi G.C. et al., Crystal forms of rifaximin and their effect on pharmaceutical properties., CrystEngComm 10, pp. 1074-1081 (2008).
Alvisi V. et al., Treatment of secretory diarrhoeas. A double-blind trial of the effectiveness of rifaximin (L 105) and neomycin., Clin. Trials J., 21 (4), pp. 215-223 (1984).
Jiang Z.D. et al., Rifaximin-induced alteration of virulence of diarrhoea-producing *Escherichia coli* and Shigella sonnei., Int. J. Antimicrob. Agents, 35 (3) pp. 278-281 (2010).
Kibbe A.H., Handbook of pharmaceutical Excipients., American Pharm. Association and Pharm. Press, 165,. p. 442 (2000).
Braga D et al., The Structure-Property Relationship of Four Crystal Forms of Rifaximin, CrystEngComm 14, pp. 6404-6411, (2012).
Non-Final Office Action issued by the US Patent and Trademark Office dated May 11, 2010 in U.S. Appl. No. 11/814,628, filed Jul. 24, 2007 in the name of Giuseppe Claudio Viscomi et al.
Response to Non-Final Office Action dated Nov. 10, 2010 in U.S. Appl. No. 11/814,628, filed Jul. 24, 2007 in the name of Giuseppe Claudio Viscomi et al.
Non-Final Office Action issued by the US Patent and Trademark Office dated Mar. 31, 2011 in U.S. Appl. No. 11/814,628, filed Jul. 24, 2007 in the name of Giuseppe Claudio Viscomi et al.
Response to Non-Final Office Action dated Sep. 30, 2011 in U.S. Appl. No. 11/814,628, filed Jul. 24, 2007 in the name of Giuseppe Claudio Viscomi et al.
Final Office Action issued by the US Patent and Trademark Office dated Dec. 13, 2011 in U.S. Appl. No. 11/814,628, filed Jul. 24, 2007 in the name of Giuseppe Claudio Viscomi et al.

(56) References Cited

OTHER PUBLICATIONS

Response to Final Office Action dated Mar. 12, 2012 in U.S. Appl. No. 11/814,628, filed Jul. 24, 2007 in the name of Giuseppe Claudio Viscomi et al.
Non Final Office Action dated Nov. 20, 2012 in U.S. Appl. No. 11/814,628, filed Jul. 24, 2007 in the name of Giuseppe Claudio Viscomi et al.
Applicant Interview Summary dated Dec. 28, 2012 in U.S. Appl. No. 11/814,628, filed Jul. 24, 2007 in the name of Giuseppe Claudio Viscomi et al.
Applicant Interview Summary dated Apr. 17, 2013 in U.S. Appl. No. 11/814,628, filed Jul. 24, 2007 in the name of Giuseppe Claudio Viscomi et al.
Response to Non-Final Office Action submitted May 20, 2013 in U.S. Appl. No. 11/814,628, filed Jul. 24, 2007 in the name of Giuseppe Claudio Viscomi et al.
Non-Final Office Action issued by the US Patent and Trademark Office dated Jul. 21, 2011 in U.S. Appl. No. 12/439,094, filed Feb. 26, 2009 in the name of Paola Maffei et al.
Response to Non-Final Office Action dated Jan. 21, 2012 in U.S. Appl. No. 12/439,094, filed Feb. 26, 2009 in the name of Paola Maffei et al.
Non-Final Office Action issued by the US Patent and Trademark Office dated Mar. 1, 2013 in U.S. Appl. No. 13/544,945, filed Jul. 9, 2012 in the name of Paola Maffei et al.
Response to Non-Final Office Action dated Sep. 3, 2013 in U.S. Appl. No. 13/544,945, filed Jul. 9, 2012 in the name of Paola Maffei et al.
Final Office Action issued by the US Patent and Trademark Office dated Oct. 2, 2013 in U.S. Appl. No. 13/544,945, filed Jul. 9, 2012 in the name of Paola Maffei et al.
Non-Final Office Action issued by the US Patent and Trademark Office dated Oct. 11, 2013 in U.S. Appl. No. 13/238,739, filed Sep. 21, 2011 in the name of Giuseppe Claudio Viscomi.
International Search Report and Written Opinion dated Dec. 21, 2007 as issued in PCT/IB2007/002199 filed Jul. 31, 2007 in the name of Paola Maffei et al.
Communication from the Examining Division dated Jan. 16, 2013 as issued on EP 07804680.2 filed on Jul. 31, 2007 in the name of Paola Maffei et al.
International Search Report mailed by European Patent Office dated Nov. 25, 2011 for the application N. PCT/IB2011/054133 filed on Sep. 21, 2011 in the name of Alfa Wassermann S.p.A.
International Preliminary Report on Patentability, issued by ISA, dated Mar. 26, 2013 for the application N. PCT/IB2011/054133 filed on Sep. 21, 2011 in the name of Alfa Wassermann S.p.A.
Prior Search Results for ITBO20100567 provided by European Patent Office dated Apr. 23, 2013 for the application EP11776879.6 filed on Sep. 21, 2011 in the name of Alfa Wassermann S.p.A.
Amendment filed by Applicant before the examination, to European Patent Office dated Oct. 25, 2013 for the application EP11776879.6 filed on Sep. 21, 2011 in the name of Alfa Wassermann S.p.A.
Communication issued by the Examination Division of the European Patent Office dated Nov. 7, 2011 in EP06723226.4 filed on Mar. 6, 2006 in the name of Alfa Wassermann S.p.A.
Communication issued by the Examination Division of the European Patent Office dated May 21, 2012 in EP06723226.4 filed on Mar. 6, 2006 in the name of Alfa Wassermann S.p.A.
Response to Final Rejection dated Jan. 29, 2014 in U.S. Appl. No. 13/544,945, filed Jul. 9, 2012 in the name of Paola Maffei et al.
Communication issued by the European Patent Office dated Nov. 17, 2014 for the application EP07804680.2 filed on Jul. 31, 2007 in the name of Alfa Wassermann S.p.A.
Observations by third parties in respect of the application EP07804680.2 filed on Jul. 31, 2007 in the name of Alfa Wassermann S.p.A.
G2/88 Decision of Enlarged BoA , Documents cited in the observation by third parties in respect of the application EP07804680.2 filed on Jul. 31, 2007 in the name of Alfa Wassermann S.p.A.
Restriction Requirement issued by the US Patent and Trademark Office dated Nov. 20, 2009 in U.S. Appl. No. 11/814,628, filed Jul. 24, 2007 in the name of Giuseppe Claudio Viscomi et al.
Restriction Requirement issued by the US Patent and Trademark Office dated Sep. 28, 2012 in U.S. Appl. No. 12/695,945, filed Jan. 28, 2010 in the name of Giuseppe Claudio Viscomi et al.
Restriction Requirement issued by the US Patent and Trademark Office dated Jun. 17, 2015 in U.S. Appl. No. 14/044,844, filed Oct. 2, 2013 in the name of Alfa Wassermann S.p.A.s.
Restriction Requirement issued by the US Patent and Trademark Office dated Nov. 26, 2010 in U.S. Appl. No. 12/439,094, filed Feb. 26, 2009 in the name of Paola Maffei et al.
Communication issued by the European Patent Office dated Jun. 23, 2015 for the application EP07804680.2 filed on Jul. 31, 2007
International Preliminary report on patentability dated Dec. 15, 2008 as issued in PCT/IB2007/002199 filed on Jul. 31, 2007 in the name of Alfa Wassermann S.p.A.
"Disintegration of Tablets and Capsules", European Pharmacopoeia 6.3, Jan. 1, 2008. pp. 3943-3945.
Normix Label (Italian with English translation), Documents cited in the observation by third parties in respect of the application EP07804680.2 filed on Jul. 31, 2007 in the name of Alfa Wassermann S.p.A.
Normix Label (Czech with English translation), Documents cited in the observation by third parties in respect of the application EP07804680.2 filed on Jul. 31, 2007 in the name of Alfa Wassermann S.p.A.
Li et al. "Solvothermal Growth of Vaterite in the Presence of Ethylene Glycol, 1,2-Propanediol and Glycerin" Journal of Crystal Growth; Mar. 2002; vol. 236,No. 1; pp. 357-362.
Uresti et al., "Effect of sugars and polyols on the functional and mechanical properties of pressure-treated arrowtooth flounder (*Atheresthes stomias*) proteins" Food Hydrocolloids; 2005; vol. 19; pp. 964-973.
Vippagunta et al. "Crystalline solids" Advanced Drug Delivery Reviews; May 2001; vol. 48; No. 1; pp. 3-26.
Tibble, A simple method for assessing intestinal inflammation in Crohn's disease, Oct. 4, 2000, 506-5013, 47.
MacCaferri et al., Rifaximin modulates the colonic microbiota of patients with Crohn's disease: an in vitro approach using continuous culture colonic model system, Sep. 18, 2010, 2556-2565.
Remington, Fluid-bed granulation method 18○ED, Jan. 1, 1990, 1644.
Kibbe A.H., Propylene glycol—Handbook of pharmaceutical Excipients 3 Ed, Jan. 15, 2000, 442.
Rowe et al., Propylene glycol—Handbook of Pharmaceutical Excipients, 5th edition, Jan. 1, 2006, 624-626.
Rowe, Mannitol—Handbook of Pharmaceutical Excipients, 5th edition, Jan. 1, 2006, 449-453.
Rowe et L., Erythritol—Handbook of Pharmaceutical Excipients, 5th edition, Jan. 1, 2006, 266-267.
Pimentel et al., The Effect of a Nonabsorbed Oral Antibiotic (Rifaximin) on the Symptoms of the Irritable Bowel Syndrome, Oct. 1, 2006, 557-563, 145(8), Ann. Intern, Med.
Fumi et al., Rifaximin treatment for symptoms of irritable bowel syndrome, Feb. 26, 2008, 408-412, 42(3), Annals of Pharmacotherapy.
EPO Communication pursuant to Article 94(3) of Jan. 16, 2013.
Response filed by the Applicant dated Mar. 25, 2013 to the Examination Division for the Application N. EP07804680.2. 6 pages.
Observations by third parties in respect of the application EP07804680.2 filed on Mar. 20, 2015. 2 pages.
SPC (Summary of product characteristics) of the market product normix in Italy, Aug. 2009, 20 pages.
SPC (Summary of product characteristics) of the market product normix in Czech, Sep. 2003, 7 pages.
EPO Communication pursuant to Article 94(3) dated Jun. 23, 2015.
Response filed by the Applicant dated Oct. 7, 2015 to the Examination Division for the Application N. EP07804680.2. 8 pages.
Observations by third parties in respect of the application EP07804680.2 filed on Jan. 19, 2016. 2 pages.
ICH Guidelines Q6a Jun. 10, 1999(International Conference on Harmonisation of Technical Requirements for Registration of Pharmaceuticals for Human Use).

(56) References Cited

OTHER PUBLICATIONS

Observations by third parties in respect of the application EP07804680.2 filed on May 2, 2016. 2 pages.
US-FDA Label of Xifaxan 200 mg tablets May 21, 2004, 13 pages.
Zaxine SmPC Sep. 2000, 10 pages.
Summons to attend Oral Proceedings issued on May 23, 2016 for the Application N. EP07804680.2. 6 pages.
Response to the summons to attend Oral Proceedings filed by the Applicant on Oct. 14, 2016 for the Application N. EP07804680.2.33 pages.
Film coating materials and their properties—Pharmapedia (http://pharmapedia.wikidot.com/film-coating-materails -and-their-properties [Sep. 20, 2016] 10:47:42, 24 pages.
European Commission—A guideline on Summary of Product Characteristics (smPC), Sep. 2009, 29 pages.
Viscomi et al. (2008) "Crystal forms of rifaximin and their effect on pharmaceutical properties" *CryestEngComm* 10:1074-1081.
Observations by third parties in respect of the application EP07804680.2 filed on Nov. 15, 2016. 2 pages.
Observations by third parties in respect of the application EP07804680.2 filed on Nov. 22, 2016. 2 pages.
Lactose—Some basic properties and characteristics (DFE Pharma), accessed on Dec. 13, 2016 from http://www.dfepharma.com/en/downloads.aspx?id=%7B2BB38A30-33EC-488D-9B1F-FEE0AD797636%7D, 12 pages.
Grounds of opposition filed by Zaklady Farmaceutyczne Polpharma S.A. against European Patent No. 2059232 B1. Jan. 17, 2018. 19 pgs.
Grounds of opposition filed by Sandoz Gmbh against European Patent No. 2059232 B1. Jan. 19, 2018. 23 pgs.
Grounds of opposition filed by Pentafarma Sociedade Técnico-Medicinal S.A. against European Patent No. 2059232 B1. Jan. 19, 2018. 25 pgs.
Consolidated list of documents cited in the Oppositions against EP 2 059 232, Mar. 5, 2018. 3 pages.
SPC of Normix® in Italy from 1985. Revision of 2012. 17 pgs.
SPC of Normix® in the Czech Republic in 2003. 6 pgs.
Rowe, R.C. et al., Cyclodextrins. Handbook of Pharmaceutical Excipients, 5th edition 2006, p. 217-221. 13 pgs.
Uresti, R.M. et al., Effect of sugars and polyols on the functional and mechanical properties of pressure-treated arrowtooth flounder (Atheresthes stomias) proteins, Food Hydrocolloids, 2005, 19, 964-973.
Qing Li et al., Solvothermal growth of vaterite in the presence of ethylene glycol, 1,2-propanediol and glycerin, Journal of Crystal Growth, 2002, 236, 357-362.
Viscomi, G.C. et al., Crystal forms of rifaximin and their effect on pharmaceutical properties, CrystEngComm, 10, Jan. 1, 2008, 1074-1081.
Rifaximin, printout from Wikipedia. Dec. 31, 2017. 4 pgs.
Cellulose, printout from Wikipedia. Jan. 7, 2018. 8 pgs.
Figures 1 and 5 of the opposed patent with indication of polymorph α peaks according to Ref No. 30 (Viscomi et al.). Jan. 1, 2008. 2 pgs.
Figure 4 of the opposed patent with indication of polymorph beta peaks according to Ref. No. 30 (Viscomi et al.). Jan. 1, 2008. 2 pgs.
Experimental report of process according to claim 13 of EP 2059232 B1. Jan. 11, 2018. 4 pgs.
Excerpt from European Patent Bulletin, p. 36, Feb. 2008. 1 pg.
Excerpt from European Patent Register EP 1 874 273. Jan. 16, 2018. 2 pgs.
Excerpt from the Italian Patent Register of BO 2005 A 000123. Jan. 15, 2018. 2 pgs.
Excerpt from the INPADOC patent family list of BO 2005 A 000123. Jan. 15, 2018. 1 pg.
Request for correction of figures made by defendant for International patent application No. PCT/IB2007/002199. Sep. 10, 2008. 4 pgs.
Specifications: Test Procedures and Acceptance Criteria for New Drug Substances and New Drug Products: Chemical Substances Q6A. ICH Harmonised Tripartite Guideline. International Conference on harmonization of Technical Requirements for Registration of Pharmaceuticals for Human Use, Oct. 6, 1999. 35 pgs.
Observations by third parties in respect of the application EP 17157159.9, divisional of EP 07804680.2, filed on Feb. 14, 2018. 4 pages.
SmPC of Zaxine, Sep. 2000. 10 pages.
FDA Label of Xifaxan, May 2004. 13 pages.
DailyMed entry for Xifaxan, Jan. 2018. 27 pages.
Consolidated List of Documents cited in the Opposition against EP2059232. Nov. 14, 2018. 5 pages.
Preliminary non-binding opinion of the Opposition Division (Opposition against EP 2 059 232). Jul. 12, 2018. 8 pages.
Response to the Communication of Notices of Opposition against EP 2 059 232 dated Feb. 7, 2018. Jun. 1, 2018. 36 pages.
Summons to attend Oral Proceedings pursuant to Rule 115(1) EPC (Opposition against EP 2 059 232). Jul. 12, 2018. 1 page.
Consolidated List of Documents enclosed to Response to the Communication of Notices of Opposition against EP 2 059 232 dated Feb. 7, 2018 Jun. 1, 2018. 3 pages.
W. A. Ritschel, "Die Tablette", Editio Cantor Verlag, 2nd edition 2002, pp. 28, 584. English + Italian. 11 pages.
Declaration by Prof. Grepioni regarding EP 2059232 B1, Dec. 12, 2011. 5 pages.
Declaration of UIBM concerning the advanced accessibility of Italian Patent Application No. BO2005A000123. Apr. 27, 2018. English + Italian. 2 pages.
Declaration of UIBM concerning the wrongly reported publication date of Italian Patent Application No. BO2005A000123. May 9, 2018. English + Italian. 2 pages.
Request for correction of Table 1 of Italian Patent No. 1.375.471. Dec. 29, 2010. English + Italian. 10 pages.
Extract from the Register of UIBM concerning the Italian Patent Application No. BO2005A000123. May 15, 2018. English + Italian. 8 pages.
Consolidated List of Documents cited in the Opposition against EP2618819. Nov. 14, 2018. 1 page.
Notice of Opposition against EP 2 618 819. Jul. 31, 2018. 5 pages.
Grounds of Opposition filed by Sandoz against EP 2 618 819 on Jul. 31, 2018. 19 pages.
C. Prantera et al., "Rifaximin-extended intestinal release induces remission in patients with moderately active Crohn's disease", Gastroenterology, 2012, 142, 473-481.

\* cited by examiner

GASTRORESISTANT PHARMACEUTICAL FORMULATIONS CONTAINING RIFAXIMIN

CROSS-REFERENCE TO RELATED APPLICATIONS

This application is a continuation of U.S. application Ser. No. 11/814,628 filed on Jul. 24, 2007, which in turn is a national phase entry under 35 USC 371 of PCT application PCT/EP2006/002022 filed on Mar. 6, 2006, which in turn claims priority to Italian patent application BO 2005A000123 filed on Mar. 7, 2005, each of which is herein incorporated by reference in its entirety. This application may also be related to U.S. application Ser. No. 12/695,945 filed on Jan. 28, 2010.

The object of the invention consists of pharmaceutical formulations containing rifaximin in the shape of microgranules made gastroresistant by an insoluble polymer at pH values between 1.5 and 4.0 and soluble at pH values between 5.0 and 7.5, by their preparation and by their use in the manufacture of medicinal preparations useful in the treatment of inflammatory bowel diseases (IBD) and mainly Crohn's disease.

BACKGROUND OF THE INVENTION

The intestinal apparatus is affected by many inflammatory diseases generally capped as inflammatory bowel diseases. In particular, Crohn's disease is a severe chronic inflammatory disease affecting various levels of the digestive tract, from the mouth to the anus, particularly it can be observed in the last portion of the small intestine, either the ileum, the colon or both and sometimes in the mucous membrane of the colon and in the anal region as well. In the interested intestinal part, inflammation, swelling and ulceration occur in the whole intestinal wall causing stenosis, bleeding ulcers and pain, while the non-affected tissue portions appear normal. Crohn's disease exhibits alternate periods of inflammatory symptoms of variable gravity with symptoms such as: diarrhea, abdominal pain, weight loss often accompanied by rhagades or peri-rectal fistulas. From two-thirds to three-quarters of patients with Crohn's disease require surgery at some point in their lives. Surgery is used either to relieve symptoms that do not respond to medical therapy or to correct complications such as blockage, perforation, abscess, or bleeding in the intestine.

The role of the intestinal bacterial flora in the etiopathogenesis of the intestinal inflammatory diseases and in particular in Crohn's disease is evidenced by, for example, the frequency of localization to areas with high bacteria concentrations, see Jannowitz, H. D., in Inflamm. Bowel Dis., 1998, 44, 29-39; the deviation of the faecal flow determines remission of the endoscopic damages which reappear again at restoration of the canalisation, see Rutgeerts, P., in Lancet, 1991, 338, 771-774; experimental models, e.g., knock-out mouse for the IL-10 gene or others, show that spontaneous colitis does not develop if a "germ-free" condition is maintained, see Blumberg R. S., in Curr. Opin. Immunol., 1999, 11(6), 648-56; inflammation of intestinal mucous membrane develops after the contact with faecal material, see Harper P. H., in Gut 1985, 26(3), 279-84; after surgical "curative" therapy consisting of ileocolic anastomosis, antibiotic treatment delays the development of both endoscopic and clinic relapses, see Cameron J. L. in Ann Surg., 1992, 215, 546-52; and the presence of fistulae or abscess-sacs points out further the bacterial contribution to the disease development.

Crohn's disease has previously been treated with drugs that are able to decrease or control the inflammation, e.g., cortisones, salazopirine, mesalazine, immunosupressants, specific chemotherapeutics, antibiotics and protein inhibitors of the actions of the Tumor Necrosis Factor (TNF). During the treatment of the acute phase of the inflammatory bowel disease, stronger treatments are often necessary to ensure parenteral alimentation, to reconstitute the loss of proteins, liquids and salts, to permit the intestine to rest to facilitate the cicatrisation of ulcers. The purpose of the therapy is to decrease the frequency of the reappearance of symptoms and to reduce the seriousness acute episodes when they appear. However, with current therapies, acute episodes respond in about 50-70% of the cases, but relapses occur in 80% of the patients.

Antibiotics are usually used to decrease the growth of the luminal bacteria; to decrease the inflammatory state sustained as a result of the bacterial growth; to reduce symptoms of the acute phase of the disease, e.g., diarrhea, intestinal pain and meteorism; and to prevent and to cure septic complications, e.g., abscesses, fistulas and toxic state.

The most frequently used antibiotics are systemically absorbed, for example, metronidazole (active against some parasites along with many anaerobic bacteria) and ciprofloxacin (active against such bacteria as E. Coli and aerobic enterobacteriace). Metronidrazol has been used at a dose of 10-20 mg/kg/day for 4 months (Sunterland, L. Gut, 199132, 1071-5), while ciprofloxacin has been used at a dose of 1000 mg/day for 6 weeks (Colombel J. F. in Am. J. Gastoenterol., 1999, 94, 674-8), while Prantera in Am. J. Gastoenterol., 1996, 91, 328-32, adopted the combination of the two antibiotics using metronidazole at the dose of 1000 mg/day and ciprofloxacin at the dose of 1000 mg/day for 12 weeks. The high systemic bioavailability of these antibiotics is at the root of their high incidence of side effects registered in long-term therapies, which negatively impacts their use. The incidence of side effects in the use of metronidazole ranges from 10% to 20%, depending on the dose and the treatment duration. The most frequent side-effects include metallic taste, gastric intolerance, nausea, glossitis, cephalea, vertigo, ataxia, convulsion and neurotoxicity. Peripheral neuropathy has been recorded in 50-85% of the long-term treated patients, which may regresses only after several months of therapeutic interruption. The percentage of side effects described in ciprofloxacin studies is variable and depends in part on the dosage and the duration of the treatment. The most frequent of the side effects are of gastrointestinal origin, but an increase of the transaminase and skin reactions have also been frequently described. Thus, there is a need in the art for a long-term treatment option for inflammatory diseases of the digestive tract, e.g., gastro enteric pathologies.

SUMMARY

Described herein are gastroresistant rifaximin microgranules and related compositions, formulations, methods and systems.

DETAILED DESCRIPTION

It is advantageous for pharmaceutical preparation used for treating inflammatory bowel diseases (e.g., gastro enteric pathologies) that are based on antibiotics to have one of more of the following characteristics: intestinal level activity, low absorption, bacteria level control in the intestinal lumen, wide spectrum of actions against the microbes (e.g., intestinal Gram-positive, Gram-negative, aerobic and anaerobic components), possibility of long term therapy without side effects, ease of administration to facilitate compliance even with the potential of high dosage necessity, e.g., long-term dosing and/or multiple dosing per day.

An antibiotic possessing several of these characteristics is rifaximin (INN; see The Merck Index, XIII Ed., 8304), which is characterized by a wide spectrum of action against many Gram-positive and Gram-negative bacteria, including aerobic and anaerobic bacteria. Bioavailability studies in healthy volunteers have shown that, when given orally, less than 1% of rifaximin is absorbed and it concentrates in the intestinal lumen and in the faecesas described herein (Descombe J. J. et al. *Pharmacokinetic study of rifaximin after oral administration in healthy volunteers. Int J Clin Pharmacol Res,* 14 (2), 51-56, (1994)). The absence of rifaximin absorption has been confirmed in patients affected by chronic bowel disease, (see Rizzello, Eur. J. Clin. Pharmacol. (1998) 54, 91-93). Moreover, the low absorption profile of rifaximin reduces the incidence of side effects and the unwanted risk of pharmacological interactions. Thus, rifaximin may be considered useful in the therapy of inflammatory chronic bowel disease and particularly in Crohn's disease. The potential efficacy of rifaximin in chronic inflammatory bowel diseases has been confirmed, see Gionchetti, P., Dig. Dis. Sci., 1999, 44, 1220-1, who hypothesized the use of rifaximin in patients with moderate or severe ulcerative colitis refractory to steroid-treatment.

Rifaximin has been described in Italian Patent IT 1154655 (1980) and EP 0161534 (1985), both of which are incorporated herein by reference in their entirety for all purposes. EP 016153 discloses a process for rifaximin production using rifamycin O as the starting material (The Merck Index, XIII Ed., 8301).

Guidance for rifaximin crystallisation and drying are described in Italian Patent Application No. MI2003A002144 (2003), in European Patent Application No. EP 1557421 (2003); in U.S. patent application Ser. No. 10/728,090 (2003) in PCT Patent Application No WO2005/044823; all of which are incorporated herein by reference in their entirety for all purposes. The experimental conditions described in these patents allow yielding polymorphic forms of rifaximin named Form α, Form β, Form γ, Form δ and Form ε, respectively.

Rifaximin is approved in certain countries for the treatment of pathologies whose etiology is in part or totally due to intestinal acute and chronic infections sustained by Gram-positive and Gram-negative bacteria, with diarrhea syndromes, altered intestinal microbial flora, summer diarrhea-like episodes, traveler's diarrhea and enterocolitis; pre- and post-surgery prophylaxis of the infective complications in gastro intestinal surgery; and hyperammonaemia therapy as coadjutant. Rifaximin is currently marketed as tablets or capsules at the dosage of 100 mg and 200 mg, in a ready to use preparation for children, or as ointment for the treatment of topical infections.

Studies on commercially available samples, particularly 200 mg tablets, have shown a potential usefulness of rifaximin in the prevention of the relapse of Crohn's disease after endoscopic resection. However, the absence of a placebo group in the clinical trial does not allow to draw confident conclusions, see Rizzello, Gut., 2000, 47, Supp. 3, A12. However, the suggested posology the use of the rifaximin 200 mg tablets has to be considered sub optimal due to the need up to six tablets a day for three months, resulting in a poor patient compliance. The 200 mg tablets of rifaximin have also been used in the treatment of Crohn's disease with dosages of 600 mg/day for 16 weeks as described by Shafran, I., Am. J. Gastroenterol., 2003, 98 (Suppl.) S-250.

Thus, there is a need in-the-art for a rifaximin pharmaceutical formulation for the treatment of infections specifically located in the intestinal tract. Previous formulations, after administration, are released and spread between the stomach and the intestine. Thus, when the rifaximin finally reaches the intestinal tract, the concentration is too low resulting in the need for increasing dosages. To maximize the therapeutic efficacy of rifaximin in the treatment of bowel diseases, new pharmaceutical formulations are provided herein and include, for example, rifaximin microgranules coated with a gastroresistant film which dissolves releasing the antibiotic only in the intestinal tract. This novel formulation maximizes contact between the active ingredient and the intestinal mucous due, in part, to the high superficial area of the microgranules. The novel formulations also allow for ease of high and low dose administration, for example, in paediatric use.

The novel gastroresistant rifaximin formulations takes advantage form the pH difference between the gastric environment (e.g., values from about 1.5 to about 4.0, depending on the state of fast or in presence of meal) and the intestinal lumen (e.g., values from 5.0 to about 7.5, depending of the tracts considered).

The novel forms also utilize the polymorphic forms of rifaximin.

The coating of pharmaceutical microgranules with gastroresistant film is a technique known by many years in the pharmaceutical field. It is generally performed in two steps: granulation and coating. Nevertheless, many active substances, including rifaximin, are characterized by a very fine particle size, for example, in case of rifaximin approximately 50% of the particles has a particle diameter between 10 μm and 40 μm. In such condition it is very difficult using conventional systems like fluid bed coating or pan technology. Very often agglomeration occurs or random blend of coated and uncoated particles is commonly obtained.

We have found, and this is an object of the invention, that it is possible to obtain enteric-coated microgranules of rifaximin by applying the fluid bed technology, which surprisingly allows in one step and at the same time to perform the wet-granulation of the powder and the coating of the formed microgranules with a polymer resistant to the gastric environment, commonly called enteric coating. With this approach the chief disadvantages of the wet-granulation and microgranule coating, which are in separate steps involved as well as the time and labour necessary to carry out the entire procedure, especially on the large scale, are minimised. This result comes from a combination between the rifaximin properties and a proper balancing the quantity of rifaximin, of enteric polymer, of plasticiser, and process parameters.

Figure 1A:
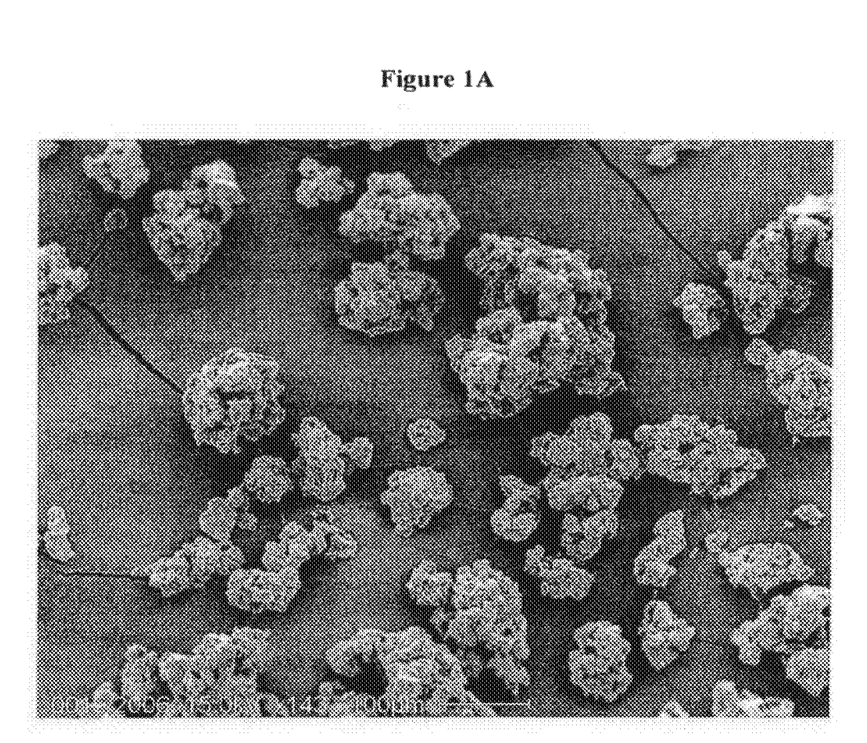
FIG. 1A is an image of rifaximin microgranules.
Figure 1B:
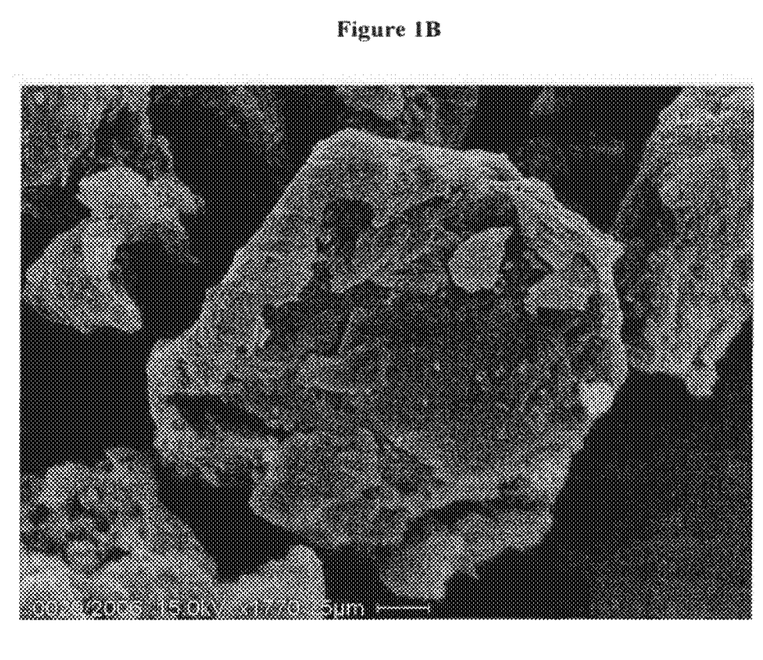
FIG. 1B is a closer image of a single rifaximin microgranule.

The efficiency of this technology in providing a complete coating layer around rifaximin is demonstrated by SEM microscopy as reported in FIGS. 1a (Scanning electron microscopy of rifaximin gastroresistant microgranules) and 1b (Scanning electron microscopy of single granule of rifaximin gastroresistant microgranules), where it is clearly show that rifaximin is fully coated by the enteric polymer. The particles sizes are quite homogeneous without large clots or very fine powder. If present, one or both of these aspects would have negative impact in any further medicinal preparation.

Figure 2:
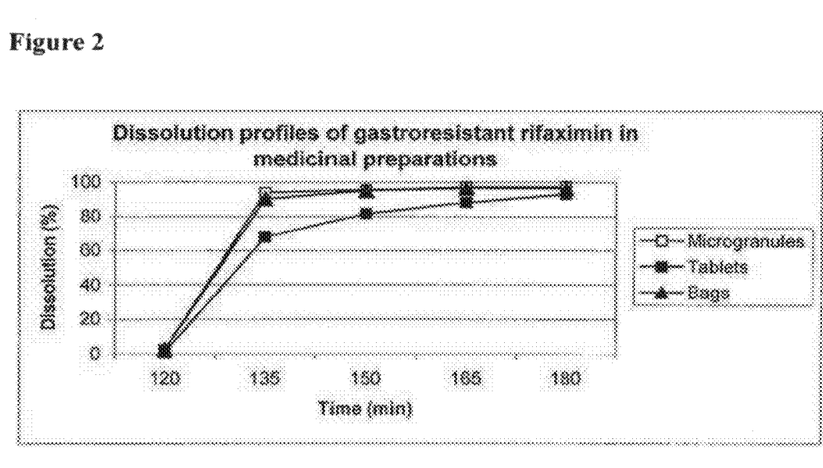
FIG. 2 is a line graph which shows the dissolution profiles of gastroresistant rifaximin microgranules.

As confirmation of the completeness of the coating, the dissolution profile of the gastroresistant microgranules of rifaximin shows that rifaximin is completely retained at low pH and released at pH higher than 5.0, as reported in FIG. 2 (Dissolution profiles).

In order to maximize the release of the active ingredient near the intestinal mucous membrane it has been utilized high pH difference between the gastric environment, values from 1.5 to 4.0, depending on the state of fast or in presence of meal and the intestinal lumen, values from 5.0 to 7.5 depending of the tracts considered. For this purpose, enteric polymeric materials having the property to solubilize at pH values between 5.0 and 7.5 have been used, to include: methacrylic acid copolymers with an acrylic or methacrylic ester like methacrylic acid ethylacrylate copolymer (1:1) and methacrylic acid methylmethacrylate copolymer (1:2), polyvinyl acetate phthalate, hydroxypropyl cellulose acetate phthalate and cellulose acetate phthalate, products available on the market for example with the trademarks KOLLICOAT®, EUDRAGIT®, AQUATERIC®, AQOAT®.

The application of these gastroresistant films to rifaximin powder or granules is performed with conventional apparatus for fluid-bed coating technology. The film coating, dissolved in organic solvents or suspended in water, is applied by spraying on powders or granules maintained in suspension with air in fluid bed systems. The most used organic solvents are: methylene chloride, methyl alcohol, isopropyl alcohol, acetone, tri-ethyl acetate and ethyl alcohol. Alternatively, the polymeric gastroresistant material can be applied suspended in water. This technique is preferable because it doesn't need the use of solvents and so it avoids the toxicological and safety related problems.

Other excipients with anti-agglomerative properties, like talc; plasticizing properties, like acetilated glycerides, diethylphthalate, propylene glycol and polyethylene glycol; surfactants like polysorbate and polyoxyethylenate esthers, anti-foam as well as anti-sticking agents can be added together with the polymeric material.

The successful application of the above mentioned technology to the coating of rifaximin powder is remarkable because it is not in the state-of-art of fluid-bed technology to spray the enteric polymer directly on the active ingredient without any preliminary treatment like granulation or layering the active ingredient on inert particles. Indeed, several drawbacks could occur without any powder pre-treatment such as large clamp formation, large range of particle diameter, inhomogeneous composition of microgranules, no uniform coating layer. The occurrence of some of these drawbacks is common with rifaximin, the powder of which is composed by a fine particles, and is extremely hydrophobic, electrostatic, hygroscopic and difficult to be mixed with common excipients in powder. Moreover it has a predisposition to segregate not allowing homogenous mixture. In presence of such unfavourable characteristics to get coated rifaximin would require the use of more than one step and a large quantity of excipients, which would limit the pharmaceutical strengths of human dosage.

As further advantage of the present invention, the gastroresistant microgranules of rifaximin prepared on the basis of the described technology of the present invention can directly be used to fill capsules or can be mixed with excipients and sweetener enhancers giving the possibility of an aqueous suspension administration.

In addition and more remarkably the gastroresistant microgranules of rifaximin can also be directly used for tablet preparation through direct compression technology by adding conventional vehicles or carriers. As additional advantage, the tablets can be scored in order to modulate the dose strength or to be crushed to facilitate the ingestion without losing the gastroresistant property of the microgranules.

All these opportunities confer significant value to the technology described in the present invention to prepare gastroresistant microgranules of rifaximin, making it suitable for a wide modulation of dosages and pharmaceutical forms.

In conclusion, the present invention shows, with respect to other marketed rifaximin preparations, remarkable improvements that can be summarized on the possibility to manufacture in only one steps gastroresistant microgranules of rifaximin, which remain insoluble in the stomach (e.g., at a range of pH between about 1.5 and about 4.0) and soluble in the intestine (e.g., at higher pH, for example between about 5.5 and about 7.5.), to administer high dose, targeting the maximum release of the active ingredient in the intestine and at the same time maximizing its contact with the intestinal mucous membrane because of the high superficial area of the microgranules.

The object of the present invention consists of pharmaceutical formulations containing microgranules of rifaximin coated with a gastroresistant polymer which is insoluble at pH values ranging between 1.5 and 4.0 and soluble at pH values ranging between 5.0 and 7.5, of their preparation and their use in intestinal inflammatory bowel diseases and in particular in Crohn's disease.

The microgranules may be from between about 1 micron to about 900 microns in diameter, or more preferably from between about 10 microns to about 500 microns in diameter.

The gastroresistance can be obtained using any material insoluble at pH values ranging between about 1 to about 4.9, from about 1.4 to about 4.2, or from about 1.5 and about 4.0. Suitable polymers may also be soluble at pH values ranging from between about 5.0 to about 7.0, 5.0 to about 7.5, or 5.0 and about 7.7 and above.

Polymeric materials utilized in the gastroresistant rifaximin formulations solubilize, as discussed above, at pH values consist with the intestinal lumen, for example, from between about 4.9 and about 7.7, and can be used as gastroresistant, entero-soluble coatings for drug release in the intestine when desired. Examples of suitable polymeric materials include, for example, acrylic polymers, methacrylic acid copolymers with an acrylic or methacrylic ester (e.g., methacrylic acid ethylacrylate copolymer (1:1) and methacrylic acid methylmethacrylate copolymer (1:2), polyvinyl acetate phthalate, hydroxypropyl cellulose acetate phthalate and cellulose acetate phthalate), as well as cellulose acetate phthalate, hydroxypropyl methylcellulose phthalate, polyvinyl acetate phthalate. Commercially available products include, for example, KOLLIKOAT®, EDRAGIT® (e.g., EUDRAGIT 40), AQUATERIC®, AQOAT®.

The enteric materials, which are soluble at higher pH values, are frequently used for colon-specific delivery systems and are employable in the gastroresistant rifaximin formulations described herein. The enteric polymers used can also be modified by mixing with other coating products that are not pH sensitive. Examples of such coating products include, for example, the neutral methacrylic acid esters with a small portion of trimethylammonioethyl methacrylate chloride, sold currently under the trade names EUDRAGIT® and EUDRAGIT® RL; a neutral ester dispersion without any functional groups, sold under the trade names EUDRAGIT® NE30D and EUDRAGIT® NE30, EUDRAGIT® 40; polysaccharides, like amylose, chitosan, chondroitin sulphate, dextran, guar gum, inulin and pectin; and other pH independent coating products.

The polymer is from between about 5% and about 75% of the weight of the microgranule. In other embodiments, the polymer is from between about 10% and about 60%, 20% and about 55%, about 20% to about 40%, about 30% to about 80%, or 25% and about 50% of the weight of the microgranule. The weight percent of the polymer to the weight of the microgranule can depend, in part, on the polymer used, the temperature of the polymer, the formulation (e.g., bag, pill, capsule, etc.), and the pH at which the polymer is soluble.

The gastroresistant rifaximin microgranules may further comprise one or more of a diluents, plasticizer, anti-agglomerative, anti-sticking, glidants, anti-foam surfactants, or colouring substances. These, along with other polymers and coating (e.g., protective coatings, over-coatings, and films) are described below.

Suitable ingredients can be incorporated into the coating formula such as plasticizers, which include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxydised tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. Other various layers, as recognized by one of skill in the art are also envisioned. The amount of plasticizer used in the polymeric material typically ranges from about 10% to about 50%, or about 10% to about 25% for example, about 10, 20, 30, 40, or 50%, based on the weight of the dry polymer.

Optional modifying components of a protective layer which can be used over the enteric or other coatings include a water penetration barrier layer (semi-permeable polymer) which can be successively coated after the enteric or other coating to reduce the water penetration rate through the enteric coating layer and thus increase the lag time of the drug release. Coatings commonly known to one skilled in the art can be used for this purpose by coating techniques such as fluid bed coating using solutions of polymers in water or suitable organic solvents or by using aqueous polymer dispersions. For example, useful materials include cellulose acetate, cellulose acetate butyrate, cellulose acetate propionate, ethyl cellulose, fatty acids and their esters, waxes, zein, and aqueous polymer dispersions such as EUDRAGIT® RS and RL 30D, EUDRAGIT® NE 30D, EUDRAGIT® 40, AQUACOAT®, SURELEASE®, cellulose acetate latex. Combinations of the polymers and hydrophilic polymers such as hydroxyethyl cellulose, hydroxypropyl cellulose (KLUCEL®, Hercules Corp.), hydroxypropyl methylcellulose (METHOCEL®, Dow Chemical Corp.), polyvinylpyrrolidone may also be used.

Anti-foaming agents can also be included in the gastroresistant rifaximin formulations. In one embodiment, the anti-foaming agent is simethicone. The amount of anti-foaming agent used typically comprises from 0% to 0.5% of the final formulation. Other agents can be added to improve the processability of a sealant or barrier layer. Such agents include, for example, talc, colloidal silica, polyvinyl alcohol, titanium dioxide, micronized silica, fumed silica, glycerol monostearate, magnesium trisilicate, and magnesium stearate, or a mixture thereof.

The amount of polymer to be used in the gastroresistant formulations is typically adjusted to achieve the desired drug delivery properties, including the amount of drug to be delivered, the rate and location of drug delivery, the time delay of drug release, and the size of the multiparticulates in the formulation. The combination of all solid components of the polymeric material, including co-polymers, fillers, plasticizers, and optional excipients and processing aids, typically provides about 1% to about 50% weight of the core.

The gastroresistant rifaximin microgranules comprise rifaximin in a polymorphous form and/or a raw form. The forms in any microgranule may be a mixture or may be a pure form. The form of rifaximin may depend, in part, on the form of the rifaximin that is coated, on the composition of excipients, and on the process used to form the microgranules. The rifaximin polymorphous forms are selected from Form α, Form β, Form γ, Form δ, or Form ε of rifaximin, mentioned above.

The mixture containing the gastroresistant material is prepared by suspending the components in demineralised water and homogenizing the suspension with an high speed mixing system, preferably an Ultra Turax homogeniser, in order to obtain a homogeneous suspension containing between 15% and 30% of solid particles. The homogeneous suspension containing the gastroresistant material can be applied by means of a coating system or a fluid bed apparatus.

In the current invention, fluid bed technology has been used. The mixture containing the active ingredient is maintained in suspension by a flux of warm air, at the same time the gastroresistant suspension is sprayed by means of a jet applied in a top part (top spray) or in a low part (bottom Spray—Wurster system) of the apparatus. For example, a fluid bed apparatus type Glatt GPG 30 has been used with a Wurster system of 18 inch with a 1.8 mm spray jet.

Process parameters including the air entering temperature, the product temperature and the speed of film application are specifically controlled. The speed of film application and the air temperature are balanced to avoid overheating of the product resulting in a non-homogeneous gastroresistant microgranule formation (too fast drying of the product) or, an agglomeration of the mixture to be coated to slow drying of the product.

In formulating, for example, a 25 kg batch of gastroresistant rifaximin, a jet spray between 150 and 300 g/min may be used. A jet spray 150 and 250 g/min, and pressures between 1.0 and 1.5 bar may also be used. The speed and pressure may be independently manipulated. The product temperature, during the spraying is maintained at a constant temperature between about 20° C. and about 40° C. The air temperature in entrance may also be regulated at between about 40° C. and about 75° C., preferably between about 60° C. and about 70° C.

The obtained gastroresistant microgranules are formulated for medical preparations in order to obtain, after adding water, a suspension with pleasant taste for the patients. Sweeteners agents like: sucrose, sorbitol, mannitol, saccharine, acesulfame, neohesperedine; suspending agents like polyvinyl pyrrolidone (PVP), sodium carboxymethyl cellulose, pectin, xantan gum, agar and glidants like silica gel can be added to the gastroresistant microgranules to this end.

The gastroresistant microgranules are mixed with the above mentioned excipients in a suitable apparatus like a biconical mixer or V mixer for the time necessary to obtain the homogeneity of the gastroresistant microgranules inside the mixture. The ratio between gastroresistant microgranules and excipients is between 1:0.1 and 1:10, preferably between 1:0.5 and 1:5. The obtained mixture can be divided in bags containing a quantity of rifaximin between 1 mg and 3000 mg, preferably between 50 mg and 800 mg.

The obtained gastroresistant microgranules of rifaximin can be directly compressed in tablet after having mixed with appropriate excipients such as diluents such as dicalcium phosphate, calcium sulphate, cellulose, microcrystalline cellulose (AVICEL®), hydroxypropyl methyl cellulose, corn starch, lactose, kaolin, mannitol, sodium chloride, dry starch; binders such as starch, gelatine, sugars as sucrose, glucose, dextrose, lactose, synthetic gum, sodium alginate, carboxymethyl cellulose, methylcellulose, polyvinylpyrrolidone, polyethylene glycol, ethylcellulose, water, waxes, alcohol; lubricants such as talc, magnesium stearate, calcium stearate, stearic acid, hydrogenated vegetable, oils, polyethylenglycole; glidants such as colloidal silicon dioxide, talc; disintegrants such as corn and potato starch, croscarmelose, crospovidone, sodium starch glycolate, colouring agents, sweeteners such as sucrose, sorbitol, mannitol, saccharine, acesulfame, neohesperedine.

Conventional technology and apparatus known to expert-of-art of tablet preparation can be applied. The gastroresistant microgranules are mixed with the above mentioned excipients in a suitable apparatus like a biconical mixer or V mixer for the time necessary to obtain the homogeneity of the gastroresistant microgranules inside the mixture.

The gastroresistant granules of rifaximin have good properties with respect to the ability to flow freely, cohesiveness and lubrication, therefore the ratio between gastroresistant micro granules and excipients is between 1:0.2 and 1:0.05, preferably between 1:0.15 and 1:0.1. The obtained mixture can be pressed in order to obtain, using a suitable punch, tablets containing a quantity of rifaximin between 50 mg and 600 mg, preferably between 100 mg and 500 mg. As described above the favorable properties of Rifaximin gastroresistant microgranules allow achieving a suitable blend for direct compression with the addition of minimal quantity of excipients. The possibility to obtain tablets using a blend containing up to 93% of gastroresistant microgranules presents a further advantage: it allows to maintain the dose of 400 mg in a suitable size to maintain a good compliance for the patient.

Tablets can be successively coated with a conventional hydrophilic film to achieve taste-masking properties and improve appearance. Suitable materials could be: hydroxyethyl cellulose, hydroxypropyl cellulose (KLUCEL®, Hercules Corp.), hydroxypropyl methylcellulose (METHOCEL®, Dow Chemical Corp.), polyvinylpyrrolidone.

The tablet containing rifaximin gastroresistant microgranules can be film-coated following conventional procedures known to someone skilled in the art selecting as a polymer one or more of cellulose and its substitutes such as hydroxypropyl cellulose, hydroxymethyl cellulose, hydroxypropylmethyl cellulose. Alternatives to the cellulose ethers are certain acrylics, such as methacrylate and methylmethacrylate copolymers. Polymers can be employed as solutions either aqueous or organic solvent-based system. Incorporating a plasticiser the flexibility of the coating film is improved; by addition of plasticisers it is reduced the risk of film cracking and it is improved the adhesion of the film to the substrate. Examples of typical plasticisers include glycerin, propylene glycol, polyethylene glycols, triacetin, acetylated monoglycerides, citrate esters and phthalate esters. Colorants usually are used to improve the appearance of the product. Water-soluble and/or organic solvent-soluble dyes can be used like albumin lake, titanium dioxide, iron oxide. Finally, stabilisers such as EDTA can be added to the coating.

Figure 3:
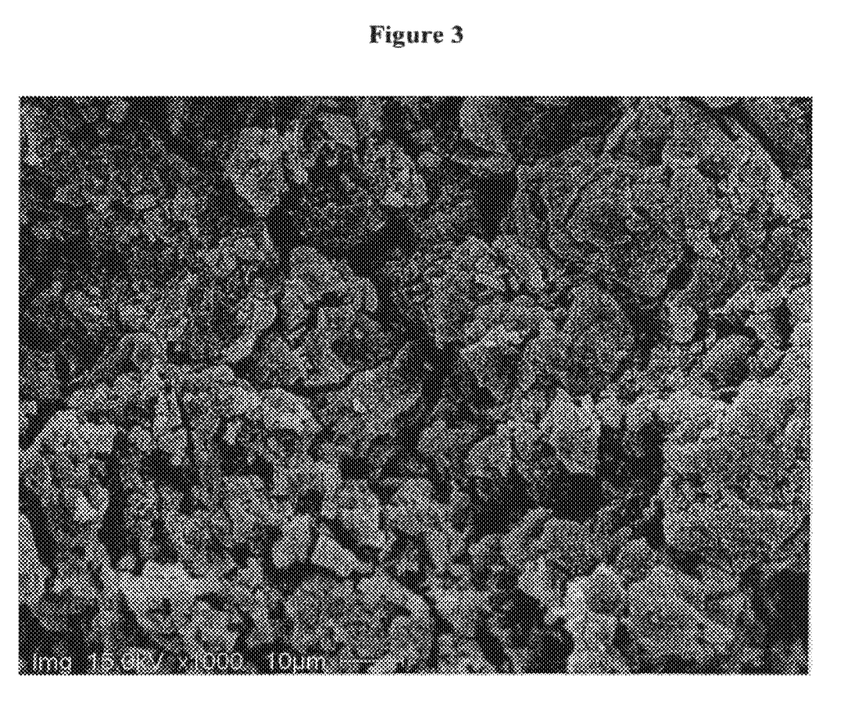
FIG. 3 is a scanning electron microscope image of gastroresistant rifaximin microgranules that are compressed in tablets.

The picture shown in FIG. 3 (Scanning electron microscopy of rifaximin gastroresistant microgranules compressed in the tablets) and the data of FIG. 2 show that the compression does not alter the integrity of the gastroresistant layer of the microgranules compressed in the tablets.

Furthermore, the obtained gastroresistant microgranules of rifaximin have such favourable properties regarding the particle size and the capacity of flow freely to be directly used, with the addition of inert diluents and glidants to fill in hard gelatine capsules. Examples of typical diluents include dicalcium phosphate, calcium sulphate, cellulose, microcristallyne cellulose, hydroxypropylmethylcellulose, corn starch, lactose, caolin, mannitol, sodium chloride, dry starch, from between about 1 and to about 225 mg. In this case the density of gastroresistant microgranules, between 0.25 and 0.45 mg/ml allows to fill about 140-250 mg of Rifaximin in conventional 000 hard gelatine capsules according to the content of Rifaximin in the gastroresistant microgranules.

All the medicine preparation, namely thermo welded bags, tablets and capsules can be usefully used in the therapy of inflammatory bowel disease to include Crohn's disease.

The following examples have to be considered as a further illustration of the object of the invention and not as a limitation.

EXAMPLE 1

Rifaximin Preparation in Gastroresistant Microgranules

In a fluid bed apparatus, Glatt GPC 30, with a Wurster system of 18 inches with a 1.8 mm spray jet, 25000 g of rifaximin powder and 125 g of Aerosil as fluidiser are loaded. Contemporaneously in a mixer under agitation a suspension is prepared using 48107 g of demineralised water, 9281 g of methacrylic acid ethylacrylate copolymer marketed under the trademark KOLLICOAT® MAE 100 P, 1392 g propylglycol, 2475 g of talc, 557 g of titanium dioxide FU and 62 g of iron oxide E 172. The solid components of the suspension are homogeneously mixed in demineralised water with an high speed homogeniser (Ultra Turrax). The prepared suspension feeds the spray system of the fluid bed apparatus and nebulized, at a pressure between 1.0 and 1.5 bar, trough the 1.8 mm nozzle on the mixture of rifaximin powder and Aerosil 200 maintained in suspension in the fluid bed by a warm air flow.

The applied conditions are described in table 1:

TABLE 1

| Process parameters | Pre-warm phase | Application of coating solution | Drying |
|---|---|---|---|
| Air flow in entrance (m³/hour) | 400 ± 100 | 550 ± 100 | 350 ± 50 |
| Air temperature in entrance (° C.) | 60 ± 2 | 60° C. ± 10 | 50 ± 2 |
| Product temperature (° C.) | 32 | 25-27 | 30 ± 2 |
| Jet pressure (bar) (initial phase) | | 1-1.5 ± 0.1 | |
| Jet speed (g/min) | | 150-200 | |

The obtained microgranules are submitted to granulometry analysis by Light Scattering technology using Malvern Mastersizer 2000 apparatus obtaining the following results:
100%<200 micron
99.17%<150 micron
90.03%<100 micron
48.37%<50 micron
6.20%<10 micron The rifaximin in the gastroresistant microgranule preparation corresponds to 61.4% of the total particle weight.

EXAMPLE 2

SEM Microscopy of Gastroresistant Microgranules of Rifaximin

A SEM Philips 515 instrument is used for the observations.

Rifaximin gastroresistant microgranules are sputtered with gold by current stream of 30 mA, getting an Au-layer of about 100 nm. An accelerating voltage of 15 kV is applied.

The images are digitally recorded with a CCD camera.

An image of microgranules of rifaximin is shown in FIG. 1A, while in FIG. 1B a detail of a single microgranule is shown.

EXAMPLE 3

Gastroresistant Microgranules of Rifaximin Prepared in Thermo Welded Bags 9.12 Kg of gastroresistant rifaximin microgranules prepared according to the example 1, 19.58 Kg of sorbitol, 0.49 Kg of aspartame, 0.21 Kg of anhydrous citric acid, 2.10 Kg of pectin, 2.10 Kg of mannitol, 0.21 Kg of neohesperidine DC, 1.12 Kg of cherry flavour and 0.07 Kg of silica gel are sieved on a sieve with mesh of 0.5 mm and then mixed for 20 minutes in a V mixer. The resulting mixture is divided in thermo welded bags containing 5 grams of product corresponding to 800 mg of rifaximin. In the following Table 2 the composition of the medicinal specialty, thermo welded bag, is reported:

TABLE 2

| Components | Amount (mg) | % |
|---|---|---|
| Gastroresistant rifaximin microgranules (corresponding to 800 mg of rifaximin) | 1303 | 26.06 |
| Aspartame | 70 | 1.40 |
| Anhydrous citric acid | 30 | 0.60 |

TABLE 2-continued

| Components | Amount (mg) | % |
|---|---|---|
| Pectin | 300 | 6.00 |
| Mannitol | 300 | 6.00 |
| Neohesperidin DC | 30 | 0.60 |
| Sorbitol | 2797 | 55.94 |
| Cherry-flavour | 160 | 3.20 |
| Silica gel | 10 | 0.20 |

EXAMPLE 4

Gastroresistant Microgranules of Rifaximin Prepared in Compressed Tablets 9.3 Kg of gastroresistant rifaximin microgranules prepared according to the example 1, 593 g of Sodium Starch Glycolate, 100 g of magnesium stearate are sieved on a sieve with mesh of 0.5 mm and then mixed for 20 minutes in a V mixer. The resulting mixture is compressed using a rotary tabletting machine (Fette 1200) equipped with oblong, scored 19×9 mm punches at the final weight of 718 mg (corresponding to a content of 400 mg of rifaximin).

The tablet composition is reported in Table 3.

TABLE 3

| Tablet composition | Amount mg | % |
|---|---|---|
| Rifaximin gastroresistant microgranules (corresponding to 400 mg of rifaximin) | 650.00 | 90.53 |
| sodium carboxymethylcellulose | 34.95 | 4.87 |
| Avicel PH 101 | 24.31 | 3.34 |
| Mg-stearate | 8.74 | 1.21 |
| | 718.00 | 100.00 |

The tablets are then coated, using conventional pan equipment, with a hydroxypropylmethylcellulose film in order to improve appearance and achieve taste mask properties. The unitary film composition is reported in Table 4:

TABLE 4

| Coating composition | Amount (mg) |
|---|---|
| HPMC | 14.07 |
| Titanium dioxide | 4.10 |
| Na-EDTA | 0.05 |
| Propylene glycol | 1.37 |
| Red Iron Oxide E 172 | 0.41 |

EXAMPLE 5

Gastroresistant Microgranules of Rifaximin Prepared in Hard Capsule 9.0 Kg of gastroresistant rifaximin microgranules prepared according to the example 1, are blended and sieved on 0.5 mm with 110 g of talc and 1.1 kg of lactose. The resulting mixture is introduced in hard gelatine capsules type 000 using a conventional equipment like Zanasi LZ64 at a final weight of 461.00, corresponding to a content of about 270 mg of rifaximin. The capsule composition is reported in Table 5.

TABLE 5

| Capsule composition | Amount | |
|---|---|---|
| | mg | % |
| Rifaximin gastroresistant granules (corresponding to 270 mg of rifaximin) | 406.00 | 88.01 |
| Talc | 5.00 | 1.01 |
| Lactose | 50.00 | 10.8 |

EXAMPLE 6

Dissolution Performance of Gastroresistant Microgranule of Rifaximin Medicinal Preparations The gastroresistance of the pharmaceutical preparation is evaluated according to what described at page 247 of the US Pharmacopeia (USP), $28^a$ Ed.

The dissolution test of medicinal preparations containing gastroresistant microgranules of rifaximin, described in examples 1, 3 and 4 and consisting of rifaximin gastroresistant microgranules, thermo welded bags containing rifaximin gastroresistant microgranules, and tablets containing rifaximin gastroresistant microgranules, respectively, are evaluated by using the following conditions:

Equipment: SOTAX AT7 Smart
Medium: HCl 0.1 N, pH 1; after 2 hours a phosphate buffer with 2% of Sodium Lauryl Sulphate is added to bring up the pH to 6.8
Stirring speed: 100 rpm
Temperature: 37° C.
Sampling time: 120, 135, 150, and 180 min.

The content of dissolved rifaximin is measured by a HPLC method.

The results, reported in Table 6, are the average of six measures and are expressed as percent of dissolution over the total amount of rifaximin.

TABLE 6

| Medium & pH | Time (min) | Dissolution (%) | | |
|---|---|---|---|---|
| | | Microgranules | Tablets | Bags |
| HCl 0.1N, pH 1 | 120 | 2.41 | 1.07 | 2.57 |
| Phosphate buffer, pH 6.8 | 135 | 93.8 | 67.9 | 90.3 |
| Phosphate buffer, pH 6.8 | 150 | 95.4 | 81.6 | 95.1 |
| Phosphate buffer, pH 6.8 | 165 | 97.2 | 88.1 | 96.4 |
| Phosphate buffer, pH 6.8 | 180 | 97.4 | 93.1 | 96.2 |

After 12 months of storage at 25° C. microgranules, prepared as in Example 1, show a similar dissolution profile, precisely a dissolution of 2.2% after 120 min at pH 1 in 0.1 N hydrochloric acid and of 91.1% after 60 min in phosphate buffer at pH 6.8.

EXAMPLE 7

Treatment of Crohn's Disease

The medicinal rifaximin preparation containing gastroresistant microgranules described in example 3 has been used in a clinical multi-center randomised trial versus placebo in patients affected by Crohn's disease. 55 Crohn's disease patients in acute, mild to moderate grade, phase, having CDAI (Crohn Disease Active Index) value between 200 and 300, have been recruited. The primary end point was represented by the percentage of the patients in clinic remission defined as CDAI lower than 150 points at the end of the study. The patients, randomised in two groups: group A, of 27 patients and group B of 28 patients, have been treated for 12 weeks according to the following therapeutic schemes:

Group A: rifaximin 800 mg, administrated 2 times a day for a total dosage equal to 1600 mg/die;

Group B: placebo, administrated 2 times in a day in a such quantity to correspond to the content of the dose of the active principle.

The primary end point, the clinical remission after 12 weeks of therapy, is achieved by 51.9% of the patients with the gastroresistant formulation and by 32.1% of the patient treated with placebo. Moreover only one patients of the group treated with rifaximin has been forced early to leave the clinical trial because of the therapeutic failure, while nine patients treated with placebo discontinued the treatment.

The results are summarised in Table 7

TABLE 7

| Group | Number of clinical remission | Number of therapeutic failure |
|---|---|---|
| A (rifaximin) 27 patients | 14 (51.9%) | 1 (3.4%) |
| B (placebo) 28 patients | 9 (32.1%) | 9 (32.1%) |

EXAMPLE 8

Treatment of Crohn's Patients Characterized by a Protein C Reactive Value Higher than Normal At the beginning of the treatment, 31 patients had a protein C reactive value, an index of inflammation in course, higher than normal. The patients have been divided into two groups: one of 16 treated with rifaximin and the other treated with placebo, as described in example 3.

The primary end point, the clinical remission, has been obtained in 62.5% of the patients treated with the new formulation of rifaximin and in 20.5% only of the patients treated with placebo. Moreover, none of the patients of the subgroup treated with rifaximin dropped from the study for therapeutic failure, unlike 6 of the patients of the subgroup treated with placebo.

The Table 8 shows the obtained results.

TABLE 8

| Subgroup with protein C value higher than normal values | Number of clinical remission | Number of therapeutic failure |
|---|---|---|
| 16 patients treated with rifaximin | 10 (62.5%) | 0 (0%) |
| 15 patients treated with placebo | 3 (20%) | 6 (40%) |

The incidence of side effects has been similar in the two groups confirming the excellent tolerability of the rifaximin formulation in continuous and prolonged use.

The invention claimed is:

1. A gastroresistant rifaximin microgranule comprising rifaximin microgranule directly coated with an enteric polymeric material comprising at least one polymer insoluble over a pH range of from 1.5 to 4.0 and soluble over a pH range of from 5.0 to 7.5, such that an enteric coating layer is formed around the rifaximin microgranule and the rifaximin is retained in the gastroresistant microgranule at pH lower than 4.0 and is released at pH higher than 5;

wherein the polymer is selected from acrylic polymers, cellulose acetate phthalate, hydroxypropylcellulose acetate phthalate, polyvinyl acetate phthalate and copolymers of methacrylic acid and the gastroresistant rifaximin microgranule has a diameter of from about 1 micron to about 900 microns.

2. The gastroresistant rifaximin microgranule of claim 1, wherein the gastroresistant rifaximin microgranule has a diameter of from about 10 micron to about 500 microns.

3. The gastroresistant rifaximin microgranule of claim 1, wherein the polymer is selected from methacrylic acid ethylacrylate copolymer (1:1), methacrylic acid methylmethacrylate copolymer (1:2) and combinations thereof.

4. The gastroresistant rifaximin microgranule of claim 1, wherein the amount of the polymer is between about 5% and about 75% by weight in respect to the total weight of the microgranule.

5. The gastroresistant rifaximin microgranule of claim 1, wherein the gastroresistant rifaximin microgranule further comprises diluents, plasticizer, anti-agglomerative, anti-sticking, glidants, anti-foam and/or colouring substances.

6. The gastroresistant rifaximin microgranule of claim 1, wherein the enteric polymeric material further comprises a plasticizer in an amount from about 10% to about 50% based on the weight of the dry polymer.

7. The gastroresistant rifaximin microgranule of claim 1, wherein the density of the gastroresistant rifaximin microgranule is between 0.25 and 0.45 mg/mL.

8. The gastroresistant rifaximin microgranule of claim 1, wherein the gastroresistant rifaximin microgranules comprise one or more of polymorphous forms of rifaximin, a raw form or a combination thereof.

9. The gastroresistant rifaximin microgranule of claim 8, wherein the rifaximin polymorphous forms are selected from Form α, Form β, Form γ, Form δ, or Form ε.

10. The gastroresistant rifaximin microgranule according to claim 8, wherein the polymorphous form is at least one of a Form β, a Form α, or a mixture thereof.

11. A pharmaceutical composition comprising the gastroresistant rifaximin microgranule of claim 1, together with a pharmaceutically acceptable excipient.

12. The pharmaceutical composition of claim 11, wherein the gastroresistant rifaximin microgranule and the pharmaceutically acceptable excipient are in a ratio of between 1:0.2 and 1:0.05.

13. The pharmaceutical composition of claim 11, comprising from between about 1 to about 3000 mg of the gastroresistant rifaximin microgranule.

14. The pharmaceutical composition of claim 11, wherein the gastroresistant rifaximin microgranule are present in the form of thermowelded bags, tablets or hard-gelatin capsules.

15. The pharmaceutical composition of claim 11, in the form of a thermo welded bag comprising from about 1 to about 3000 mg of said gastroresistant rifaximin microgranules; from 0 to about 450 mg of a sweetening agent; from 0 to about 50 mg of organic acid; from about 1 to about 500 mg of a suspending agent; from 0 to about 500 mg of mannitol; from 0 to about 4000 mg of sugar alcohol; from 0 to about 300 mg of a flavoring agent; and from 0 to about 100 mg of a glidant.

16. The pharmaceutical composition of claim 15, wherein the sweetening agent is selected from one or more of aspartame, sugar, xylitol, lactitol, SPLENDA®, sodium cyclamate, dextrose, fructose, glucose, lactose, sucrose, or neohesperidin DC.

17. The pharmaceutical composition of claim 15, wherein the organic acid is selected from one or more among citric acid, acetic acid, adipic acid, citric acid, fumaric acid, glutaric acid, malic acid, succinic acid, or tartaric acid.

18. The pharmaceutical composition of claim 15, wherein the suspending agent is selected from one or more among polyvinyl pyrrolidone (PVP), sodium carboxymethyl cellulose, pectin, xantan gum, or agar agar.

19. The pharmaceutical composition of claim 15, wherein the sugar alcohol is selected from one or more among lactitol, maltitol, mannitol, sorbitol, and xylitol, xanthan gum, dextrins, or maltodextrins.

20. The pharmaceutical composition of claim 15, wherein the flavoring agent is selected from one of more among fruit or vegetable flavor.

21. The pharmaceutical composition of claim 15, wherein the glidant is selected from one or more among silica gel, magnesium stearate, or talc.

22. The pharmaceutical composition of claim 11, in the form of a tablet comprising from about 50 to about 1000 mg of said gastroresistant rifaximin microgranules; from about 1 to about 500 mg of a diluent agent; from about 1 to about 500 mg of a binder agent; from about 0 to about 20 mg of a lubricant agent; from about 0 to about 20 mg of a glidant agent; from about 0 to about 200 mg of a disintegrant agent; from about 0 to about 10 mg a coloring agent; and from about 0 to about 500 mg of a sweetener agent.

23. The pharmaceutical composition of claim 22, wherein the diluent agent is selected form one or more among dicalcium phosphate, calcium sulphate, cellulose, microcrystalline cellulose (Avicel®), hydroxypropyl methyl cellulose, corn starch, lactose, kaolin, mannitol sodium chloride, or dry starch.

24. The pharmaceutical composition of claim 22, wherein the binder agent is selected from one or more among starch, gelatine, sugars as sucrose, glucose, dextrose, lactose, synthetic gum, sodium alginate, carboxymethyl cellulose, methylcellulose, polyvinylpyrrolidone, polyethylene glycol, ethylcellulose, water, waxes, or alcohol.

25. The pharmaceutical composition of claim 22, wherein the lubricant agent is selected from one or more among talc, magnesium stearate, calcium stearate, stearic acid, hydrogenated vegetable, oils, or polyethylene glycol.

26. The pharmaceutical composition of claim 22, wherein the glidant agent is selected from one or more among colloidal silicon dioxide, or talc.

27. The pharmaceutical composition of claim 22, wherein the disintegrant agent is selected from one or more among sodium carboxymethylcellulose, corn and potato starch, croscarmelose, crospovidone, or sodium starch glycolate.

28. The pharmaceutical composition of claim 22, wherein the coloring agent is selected from one or more among titanium dioxide, or iron oxide.

29. The pharmaceutical composition of claim 22, wherein the sweetener agent is selected from one or more among sucrose, sorbitol, mannitol, saccharine, acesulfame, or neohesperedine.

30. The pharmaceutical composition of claim 14, wherein the composition is a film-coated tablet wherein the film comprises:
from 0 to about 50 mg of polymers selected from one or more among cellulose and its derivatives, or acrylics;
from about 0 to about 5 mg of plasticizer agent selected from one or more glycerin, propylene glycol, polyethylene glycols, triacetin, acetylated monoglycerides, citrate esters or phthalate esters;
from about 0 to about 1 mg of a stabilizing agent; and
from about 0 to about 10 mg of coloring agent selected from one or more among albumin lake, titanium dioxide, or iron oxide.

31. The pharmaceutical composition of claim 30, wherein the polymers are selected from one or more among hydropropylcellulose, hydromethylcellulose, hydropropyl-methylcellulose, metacrylate and methylmetacrylate copolymers.

32. The pharmaceutical composition of claim 11, in the form of a hard-gelatin capsule comprising from about 50 to about 450 mg of said gastroresistant rifaximin microgranules; from about 0 to about 25 mg of a lubricant agents; and from about 1 to about 225 mg of a diluent agent.

33. The pharmaceutical composition of claim 32, wherein the lubricant agent is selected from one or more among talc, magnesium stearate, calcium stearate, stearic acid, hydrogenated vegetable, oils, and polyethylene glycol.

34. The pharmaceutical composition of claim 32, wherein the diluent agent is selected from one or more among dicalcium phosphate, calcium sulphate, cellulose, microcrystalline cellulose, hydroxypropylmethylcellulose, corn starch, lactose, caolin, mannitol, sodium chloride, and dry starch.

35. The gastroresistant rifaximin microgranule of claim 1, wherein the gastroresistant rifaximin microgranule further comprises a barrier layer over the enteric coating layer, the barrier layer comprising one or more semipermeable polymers configured to reduce water penetration through the enteric coating layer.

36. The gastroresistant rifaximin microgranule of claim 1, wherein the enteric polymeric material further comprises one or more plasticizers selected from acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxydised tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate or a mixture thereof.

37. A method of treatment of the inflammatory bowel diseases in a patient, the method comprising:
    administering the gastroresistant rifaximin microgranule of claim 1 to the patient.

38. The method of claim 37, wherein the inflammatory bowel disease is Crohn's disease.

39. The method of claim 38 wherein the patient suffering from Crohn's disease has a C-reactive protein value and wherein the value of C-reactive protein of the patient suffering from Crohn's disease is higher than a standard.

40. A method for manufacturing the gastroresitant rifaximin microgranule of claim 1, comprising:
    spraying an aqueous suspension through a nozzle under a pressure into a fluid bed apparatus in which a rifaximin mixture is kept in suspension, wherein the aqueous suspension contains an enteric polymeric material comprising at least one polymer insoluble over a pH range of from 1.5 to 4.0 and soluble over a pH range of from 5.0 to 7.5, to obtain the gastroresistant rifaximin microgranule directly coated with the enteric polymeric material,
    wherein the polymer is selected from acrylic polymers, cellulose acetate phthalate, hydroxypropylcellulose acetate phthalate, polyvinyl acetate phthalate and copolymers of methacrylic acid and the gastroresistant rifaximin microgranule has a diameter of from about 1 micron to about 900 microns.

41. The method of claim 40, wherein the spraying is performed with air entering the fluid bed apparatus at a temperature between 40° C. and 75° C.

42. The method of claim 40, wherein the rifaximin mixture comprises one or more polymorphous forms of rifaximin, a raw form or a combination thereof.

43. The method of claim 40, wherein the rifaximin comprises at least one of the one or more polymorphous forms of rifaximin is Form α, Form β, Form γ, Form δ, and/or Form ε.

44. The method of claim 40, wherein the enteric polymeric material further comprises one or more of talc, acetylated glycerides, diethylphthalate, propylene glycol, polyethylene glycol, surfactants, and anti-sticking agents.

* * * * *